(12) United States Patent
Carroll et al.

(10) Patent No.: US 11,759,646 B2
(45) Date of Patent: *Sep. 19, 2023

(54) BIOSTIMULATOR CIRCUIT WITH FLYING CELL

(71) Applicant: Pacesetter, Inc., Sylmar, CA (US)

(72) Inventors: Kenneth J. Carroll, Los Altos, CA (US); Alan Ostroff, Pleasanton, CA (US); Peter M. Jacobson, Livermore, CA (US)

(73) Assignee: Pacesetter, Inc., Sylmar, CA (US)

( * ) Notice: Subject to any disclaimer, the term of this patent is extended or adjusted under 35 U.S.C. 154(b) by 339 days.

This patent is subject to a terminal disclaimer.

(21) Appl. No.: 16/911,780

(22) Filed: Jun. 25, 2020

(65) Prior Publication Data

US 2020/0324123 A1 Oct. 15, 2020

Related U.S. Application Data

(62) Division of application No. 15/712,497, filed on Sep. 22, 2017, now Pat. No. 10,744,332, which is a
(Continued)

(51) Int. Cl.
*A61N 1/375* (2006.01)
*A61N 1/372* (2006.01)
*A61N 1/362* (2006.01)

(52) U.S. Cl.
CPC ........... *A61N 1/3756* (2013.01); *A61N 1/362* (2013.01); *A61N 1/3758* (2013.01); *A61N 1/37205* (2013.01); *A61N 1/375* (2013.01)

(58) Field of Classification Search
CPC .. A61N 1/3756; A61N 1/362; A61N 1/37205; A61N 1/3758; A61N 1/375
See application file for complete search history.

(56) References Cited

U.S. PATENT DOCUMENTS

| 3,199,503 A | 8/1965 | Roth |
| 3,212,496 A | 10/1965 | Preston |

(Continued)

FOREIGN PATENT DOCUMENTS

| EP | 0801958 A1 | 10/1997 |
| EP | 1741465 A1 | 1/2007 |

(Continued)

OTHER PUBLICATIONS

Restriction Requirement dated Nov. 17, 2022, U.S. Appl. No. 16/920,876 filed Jul. 6, 2020.

(Continued)

*Primary Examiner* — Pamela M. Bays
(74) *Attorney, Agent, or Firm* — Vierra Magen Marcus LLP

(57) ABSTRACT

A leadless cardiac pacemaker is provided which can include any number of features. In one embodiment, the pacemaker can include a tip electrode, pacing electronics disposed on a p-type substrate in an electronics housing, the pacing electronics being electrically connected to the tip electrode, an energy source disposed in a cell housing, the energy source comprising a negative terminal electrically connected to the cell housing and a positive terminal electrically connected to the pacing electronics, wherein the pacing electronics are configured to drive the tip electrode negative with respect to the cell housing during a stimulation pulse. The pacemaker advantageously allows p-type pacing electronics to drive a tip electrode negative with respect to the can electrode when the can electrode is directly connected to a negative terminal of the cell. Methods of use are also provided.

19 Claims, 4 Drawing Sheets

Related U.S. Application Data division of application No. 13/956,946, filed on Aug. 1, 2013, now Pat. No. 9,802,054.

(60) Provisional application No. 61/678,505, filed on Aug. 1, 2012.

(56) References Cited

U.S. PATENT DOCUMENTS

| | | | |
|---|---|---|---|
| 3,214,556 A | 10/1965 | Zacouto | |
| 3,218,638 A | 11/1965 | Honig | |
| 3,478,746 A | 11/1969 | Greatbatch | |
| 3,603,881 A | 9/1971 | Thornton | |
| 3,727,616 A | 4/1973 | Lenzkes | |
| 3,757,778 A | 9/1973 | Graham | |
| 3,823,708 A | 7/1974 | Lawhorn | |
| 3,830,228 A | 8/1974 | Foner | |
| 3,835,864 A | 9/1974 | Rasor et al. | |
| 3,836,798 A | 9/1974 | Greatbatch | |
| 3,870,051 A | 3/1975 | Brindley | |
| 3,872,251 A | 3/1975 | Auerbach et al. | |
| 3,905,364 A | 9/1975 | Cudahy et al. | |
| 3,940,692 A | 2/1976 | Neilson et al. | |
| 3,943,926 A | 3/1976 | Barragan | |
| 3,946,744 A | 3/1976 | Auerbach | |
| 3,952,750 A | 4/1976 | Mirowski et al. | |
| 4,027,663 A | 6/1977 | Fischler et al. | |
| 4,072,154 A | 2/1978 | Anderson et al. | |
| 4,083,366 A | 4/1978 | Gombrich et al. | |
| 4,102,344 A | 7/1978 | Conway et al. | |
| 4,146,029 A | 3/1979 | Ellinwood, Jr. | |
| 4,151,513 A | 4/1979 | Menken et al. | |
| 4,151,540 A | 4/1979 | Sander et al. | |
| 4,152,540 A | 5/1979 | Duncan et al. | |
| 4,157,720 A | 6/1979 | Greatbatch | |
| 4,173,221 A | 11/1979 | McLaughlin et al. | |
| 4,187,654 A | 2/1980 | Hepp et al. | |
| 4,210,149 A | 7/1980 | Heilman et al. | |
| 4,223,678 A | 9/1980 | Langer et al. | |
| 4,250,888 A | 2/1981 | Grosskopf | |
| 4,256,115 A | 3/1981 | Bilitch | |
| 4,296,756 A | 10/1981 | Dunning et al. | |
| 4,310,000 A | 1/1982 | Lindemans | |
| 4,318,412 A | 3/1982 | Stanly et al. | |
| 4,336,810 A | 6/1982 | Anderson et al. | |
| 4,350,169 A | 9/1982 | Dutcher et al. | |
| 5,243,977 A | 9/1993 | Trabucco et al. | |
| 5,642,014 A | 6/1997 | Hillenius | |
| 5,769,874 A | 6/1998 | Dahlberg | |
| 6,498,951 B1 | 12/2002 | Larson et al. | |
| 7,177,698 B2 | 2/2007 | Klosterman et al. | |
| 7,684,864 B2 | 3/2010 | Olson et al. | |
| 8,788,035 B2 | 7/2014 | Jacobson | |
| 8,798,745 B2 | 8/2014 | Jacobson | |
| 9,802,054 B2* | 10/2017 | Carroll | A61N 1/3758 |
| 10,744,332 B2* | 8/2020 | Carroll | A61N 1/37205 |
| 2005/0075677 A1* | 4/2005 | Ganion | A61N 1/3627 607/9 |
| 2005/0082942 A1 | 4/2005 | Shirley | |
| 2005/0136385 A1 | 6/2005 | Mann et al. | |
| 2006/0247688 A1 | 11/2006 | Olson et al. | |
| 2007/0088405 A1 | 4/2007 | Jacobson | |
| 2007/0135883 A1* | 6/2007 | Drasler | A61B 5/6848 607/126 |
| 2009/0240299 A1 | 9/2009 | Adekore et al. | |
| 2012/0116483 A1* | 5/2012 | Yonezawa | A61N 1/36 607/2 |
| 2013/0261497 A1 | 10/2013 | Pertijs et al. | |
| 2013/0274847 A1 | 10/2013 | Ostroff | |
| 2013/0324825 A1 | 12/2013 | Ostroff et al. | |
| 2014/0039570 A1 | 2/2014 | Carroll et al. | |
| 2018/0008833 A1 | 1/2018 | Carroll et al. | |
| 2020/0330773 A1* | 10/2020 | Carroll | A61N 1/3758 |

FOREIGN PATENT DOCUMENTS

| | | |
|---|---|---|
| JP | H04-506167 | 10/1992 |
| JP | 05-245215 | 9/1993 |
| JP | 06/507096 | 3/2006 |
| JP | 06/516449 | 7/2006 |
| JP | 2006/526483 | 11/2006 |
| WO | WO93/12714 A1 | 7/1993 |
| WO | WO02/34333 A2 | 5/2002 |
| WO | WO04/012811 | 2/2004 |
| WO | WO2006/065394 A1 | 6/2006 |
| WO | WO2007/047681 A2 | 4/2007 |
| WO | WO2007/059386 A2 | 5/2007 |
| WO | WO 2014/022661 A1 | 2/2014 |

OTHER PUBLICATIONS

Response to Restriction Requirement dated Jan. 10, 2023, U.S. Appl. No. 16/920,876 filed Jul. 6, 2020.
International Search Report dated Nov. 22, 2013; Related Serial No. PCT/US2013/053217.
International Searching Authority, "Notification of Transmittal of the International Search Report and the Written Opinion of the International Searching Authority, or the Declaration," International Application No. PCT/US12/63552, dated Feb. 22, 2013, 11 pages.
Notice of Allowance mailed Jul. 19, 2017; Related U.S. Appl. No. 13/956,946.
Non-Final Office Action dated Apr. 7, 2017; Related U.S. Appl. No. 13/956,946.
Amendment filed Apr. 7, 2017; Related U.S. Appl. No. 13/956,946.
Advisory Action dated Nov. 3, 2016; Related U.S. Appl. No. 13/956,946.
Amendment filed Sep. 1, 2016; Related U.S. Appl. No. 13/956,946.
Final Office Action dated Aug. 10, 2016; Related U.S. Appl. No. 13/956,946.
Amendment filed Apr. 20, 2016; Related U.S. Appl. No. 13/956,946.
Non-Final Office Action dated Jan. 21, 2016; Related U.S. Appl. No. 13/956,946.
Advisory Action dated Sep. 25, 2016; Related U.S. Appl. No. 13/956,946.
Amendment filed Sep. 25, 2015; Related U.S. Appl. No. 13/956,946.
Amendment filed Jul. 14, 2015; Related U.S. Appl. No. 13/956,946.
Final Office Action dated May 27, 2015; Related U.S. Appl. No. 13/956,946.
Amendment filed Jan. 23, 2015; Related U.S. Appl. No. 13/956,946.
Amendment filed Dec. 23, 2014; Related U.S. Appl. No. 13/956,946.
Non-Final Office Action dated Aug. 29, 2014; Related U.S. Appl. No. 13/956,946.
Restriction Requirement dated Oct. 8, 2019, U.S. Appl. No. 15/712,497, filed Sep. 22, 2017.
Response to Restriction Requirement dated Nov. 5, 2019, U.S. Appl. No. 15/712,497, filed Sep. 22, 2017.
Non-final Office Action dated Apr. 2, 2020, U.S. Appl. No. 15/712,497, filed Sep. 22, 2017.
Response to Office Action dated Apr. 29, 2020, U.S. Appl. No. 15/712,497, filed Sep. 22, 2017.
Response to Office Action dated Jun. 16, 2023, U.S. Appl. No. 16/920,876, filed Jul. 6, 2020.
Non-final Office Action dated May 4, 2023, U.S. Appl. No. 16/920,876, filed Jul. 6, 2020.

* cited by examiner

BIOSTIMULATOR CIRCUIT WITH FLYING CELL

PRIORITY CLAIM

This application is a divisional of U.S. patent application Ser. No. 15/712,497, filed Sep. 22, 2017, (issued as U.S. Pat. No. 10,744,332), which is a divisional of U.S. patent application Ser. No. 13/956,946, filed Aug. 1, 2013 (issued as U.S. Pat. No. 9,802,054), which claimed the benefit of U.S. Provisional Patent Application No. 61/678,505, filed on Aug. 1, 2012, each of which is titled "Biostimulator Circuit with Flying Cell." Priority is claimed to each of the above patent applications, the contents of each of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure relates generally to implantable pacemakers or biostimulators. More specifically, this disclosure relates to improved implantable leadless pacemakers having a reduced weight and volume.

BACKGROUND

Cardiac pacing electrically stimulates the heart when the heart's natural pacemaker and/or conduction system fails to provide synchronized atrial and ventricular contractions at appropriate rates and intervals for a patient's needs. Such bradycardia pacing provides relief from symptoms and even life support for hundreds of thousands of patients. Cardiac pacing may also give electrical overdrive stimulation intended to suppress or convert tachyarrhythmias, again supplying relief from symptoms and preventing or terminating arrhythmias that could lead to sudden cardiac death.

Pacemakers require at least two electrodes to deliver electrical therapy to the heart and to sense the intracardiac electrogram. Traditionally, pacemaker systems are comprised of an implantable pulse generator and lead system. The pulse generators are implanted under the skin and connected to a lead system that is implanted inside the heart with at least one electrode touching the endocardium. The lead system can also be implanted on the epicardial surface of the heart.

Pacemaker lead systems are typically built using a unipolar design, with an electrode at the tip of the lead wire, or bipolar design, with an additional electrode ring often 10 mm proximal to the tip electrode. Additionally, the implanted pulse generator can is often used as a pace/sense electrode. In a conventional pacemaker system, pacing occurs either between the electrode tip and ring, or between the tip and can. Likewise, sensing occurs either between the electrode tip and ring or between the tip and the can.

SUMMARY OF THE DISCLOSURE

A leadless cardiac pacemaker, comprising an electronics housing, pacing electronics disposed in the electronics housing, a tip electrode electrically coupled to the pacing electronics, a cell housing, and an energy source disposed in the cell housing, the energy source having a positive terminal electrically coupled to the pacing electronics, and a negative terminal electrically coupled to the cell housing, the pacing electronics being configured to drive the tip electrode negative with respect to the cell housing during a stimulation pulse.

In some embodiments, electrically coupling the negative terminal to the cell housing configures the cell housing to act as a can electrode.

In one embodiment, the pacing and sensing electronics comprise at least one p-type substrate.

In additional embodiments, the energy source comprises at least one lithium carbon mono-fluoride cell.

In some embodiments, the pacemaker does not include an additional housing or ring electrode disposed around the cell housing.

In one embodiment, the pacemaker is configured to provide stimulation pulses from the cell housing to the tip electrode through cardiac tissue.

In some embodiments, the pacing electronics permit the cell housing which is coupled to the negative terminal of the energy source to serve as a positive can electrode during the stimulation pulse.

In another embodiment, the pacing electronics include at least one switch that prevent the passage of current in the presence of defibrillation or electrosurgery voltages on a high terminal of the at least one switch.

A method of driving a leadless pacemaker is also provided, comprising the steps of coupling a negative terminal of a cell to a cell housing of the leadless pacemaker, coupling a positive terminal of the cell to p-type substrate pacing electronics of the leadless pacemaker, driving, with the pacing electronics, a tip electrode of the leadless pacemaker negative with respect to the cell housing during a stimulation pulse.

In one embodiment, the method further comprises the step of stimulating cardiac tissue with the stimulation pulse.

In some embodiments, the driving step comprises driving the tip electrode as a negative electrode and driving the cell housing as a positive electrode during the stimulation pulse.

A leadless cardiac pacemaker is also provided, comprising a tip electrode, pacing electronics disposed on a p-type substrate in an electronics housing, the pacing electronics being electrically connected to the tip electrode, and an energy source disposed in a cell housing, the energy source comprising a negative terminal electrically connected to the cell housing and a positive terminal electrically connected to the pacing electronics, the pacing electronics being configured to drive the tip electrode as a negative electrode and the cell housing as a positive electrode during a stimulation pulse.

In some embodiments, the energy source comprises at least one lithium carbon mono-fluoride cell.

In another embodiment, the pacemaker further comprises a fixation feature configured to affix the pacemaker to cardiac tissue.

In one embodiment, there is no separate housing disposed around the cell housing.

In another embodiment, the cell housing is configured to act as a can electrode.

In yet another embodiment, there is no separate ring or can electrode disposed around the cell housing.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
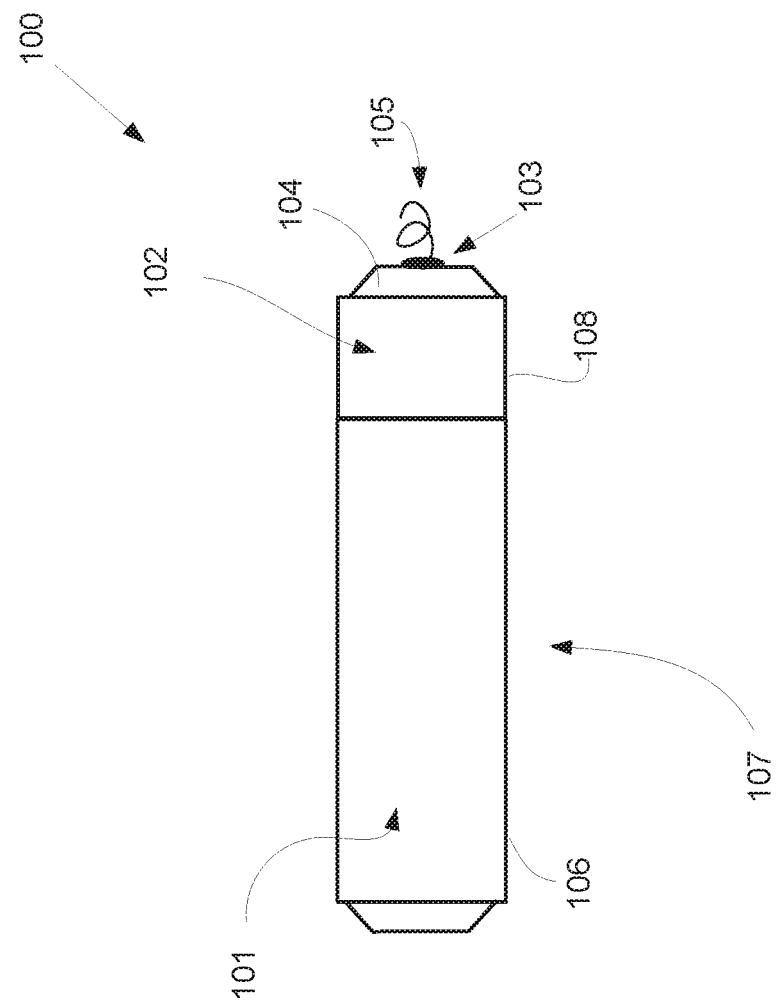
FIG. 1 shows an external view of a biostimulator or leadless pacemaker.

Leadless pacemaker designs described in the present disclosure provide improvements over conventional pacemakers with leads and also over prior leadless pacemaker designs. The leadless pacemaker designs described herein advantageously minimize biostimulator volume while increasing efficiency and cell life. Six design techniques described herein contribute to reducing biostimulator volume.

First, the housing of the device's energy source can be used as part of the housing of the stimulator. This provides more compact construction than that of conventional pacemakers, which generally include a first metal housing containing the energy source, entirely enclosed within a second metal housing containing the energy source housing, along with circuitry.

Second, an energy source with high energy per unit volume and low internal resistance can be used within the leadless pacemaker. Both features decrease the amount of reactants necessary for a specified device lifetime.

Additionally, the device's analog and digital functions can be implemented with a single integrated circuit. This reduces board area, encapsulation volume, and interconnection area, thereby allowing all the internal circuitry of the pacemaker to be contained within a smaller housing and reducing overall biostimulator volume.

Fourth, the pacemaker can have a generally cylindrical form with diameter not to exceed 7 mm, and preferably having a diameter that does not exceed 6 mm. In some embodiments, pacemakers utilizing the design of this disclosure can have dimensions of approximately 6 mm in diameter and approximately 3.5 cm in length, for a total volume of approximately 1 cc and a mass of approximately 2 gm. This enables percutaneous delivery of the biostimulator through the vasculature. To provide high energy per unit volume and low internal resistance with this form, chemical cell manufacturers propose lithium carbon monofluoride ("CFx") cells with "bobbin" construction, symmetric around the cell's long axis, with the lithium anode arranged along the cell housing's inside wall. Thus, in some embodiments the cell housing forms the cell's negative terminal ("negative can").

Another improvement includes providing efficient stimulation via a first small-surface-area electrode ("tip"), and a second large-surface-area electrode ("ring" or "can"). The small tip provides a high electric field gradient to induce stimulation. The large ring or can provides a low spreading resistance to minimize electrical losses. To prevent corrosion, arrhythmia induction, and elevated pacing thresholds, stimulators generally provide a pulse with the tip negative with respect to the can ("positive can").

Finally, another improved disclosed herein includes implementing mixed analog and digital functions on a single integrated circuit with minimal substrate area. In some embodiments, the integrated circuits used in the leadless pacemakers described herein can include only p-type processes where no point on the chip can have a voltage below the substrate voltage ("negative ground").

FIG. 1 shows an external view of a leadless pacemaker or biostimulator 100. The pacemaker 100 can comprise energy source or cell 101, pacing electronics 102, tip electrode 103, insulator 104, and fixation feature 105. Electronics 102 can include a single p-type substrate ASIC. The pacemaker 100 can comprise an outer housing 107, which in this embodiment is a combination of cell housing 106 (surrounding cell 101) and circuit housing 108 (surrounding electronics 102). The cell housing 106 can act as an electrode (e.g. a ring electrode). In some embodiments, the housings can comprise a conductive material such as titanium, 316L stainless steel, or other similar materials. The fixation feature 105 can comprise a fixation helix or other screw-like feature configured to affix the pacemaker to cardiac tissue.

In the embodiment of FIG. 1, the negative terminal of the energy source 101 can be connected to the cell housing 106, and the positive terminal of the cell can be connected to electronics 102 within circuit housing 108. By connecting the negative terminal of the energy source to the cell housing, the cell housing can then be used as a ring or can electrode for the pacemaker. Since the cell housing 106 is connected to the negative terminal of the energy source 101 so as to act as a can electrode, the combination can be referred to collectively within this disclosure as the "negative can", "can electrode", or "ring electrode". Utilizing the cell housing as the negative can allows the pacemaker 100 to be designed without requiring an additional pacemaker housing and/or ring electrode around the energy source and cell housing, which can significantly reduce the size and cost of the pacemaker.

Insulator 104 can be configured to electrically isolate tip electrode 103 from the rest of the device, including from the electronics and the negative can. The insulator 104 can include a ceramic to metal feedthrough or a glass to metal feedthrough to connect the tip electrode to electronics 102, as known in the art. The tip electrode 103 can be, for example, a raised or "button" shaped electrode disposed on a distal tip of the housing. The tip electrode can be other shapes, including square, rectangular, circular, flat, pointed, or otherwise shaped as known in the art. In additional embodiments, the electrode can be integrated into the fixation feature 105.

When the pacemaker of FIG. 1 is activated, stimulation current can flow from the cell housing 106, at positive polarity during the stimulation pulse, to tip electrode 103, at negative polarity during the stimulation pulse. Consequently the cell housing 106 also serves as the positive ring electrode during stimulation. Insulator 104 separates the cell housing (acting as a ring or can electrode) from the tip electrode 103, both physically and electrically during use. In order for the pacemaker 100 of FIG. 1 to function properly when implanted in a heart of a patient, the tip electrode 103 must be driven negative with respect to the ring or can electrode (e.g., cell housing 106) even though the cell's negative terminal is connected directly to the ring or can electrode.

Traditionally, n-type substrate technology was available to pacemaker and pacemaker designers, who could connect the positive terminal of the cell to the n-type substrate and to the ring electrode, allowing the negative terminal of the cell to create a negative voltage that would be commuted to the tip electrode. However, it is presently difficult to find n-type substrates for use in these applications, so the present invention advantageously allows the tip electrode to be driven negative with respect to the ring electrode while using a p-type substrate.

Figure 2A:
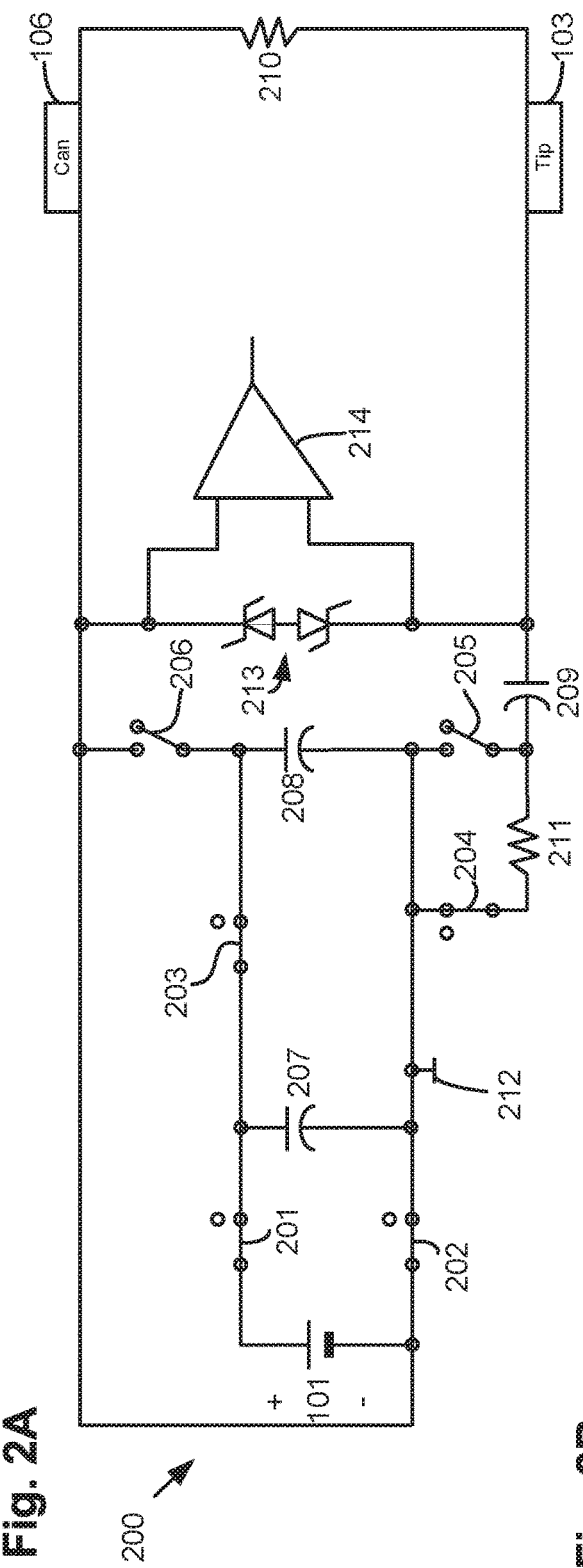
FIGS. 2A-2B provide schematic diagrams of pacing electronics according to one embodiment.
Figure 2B:
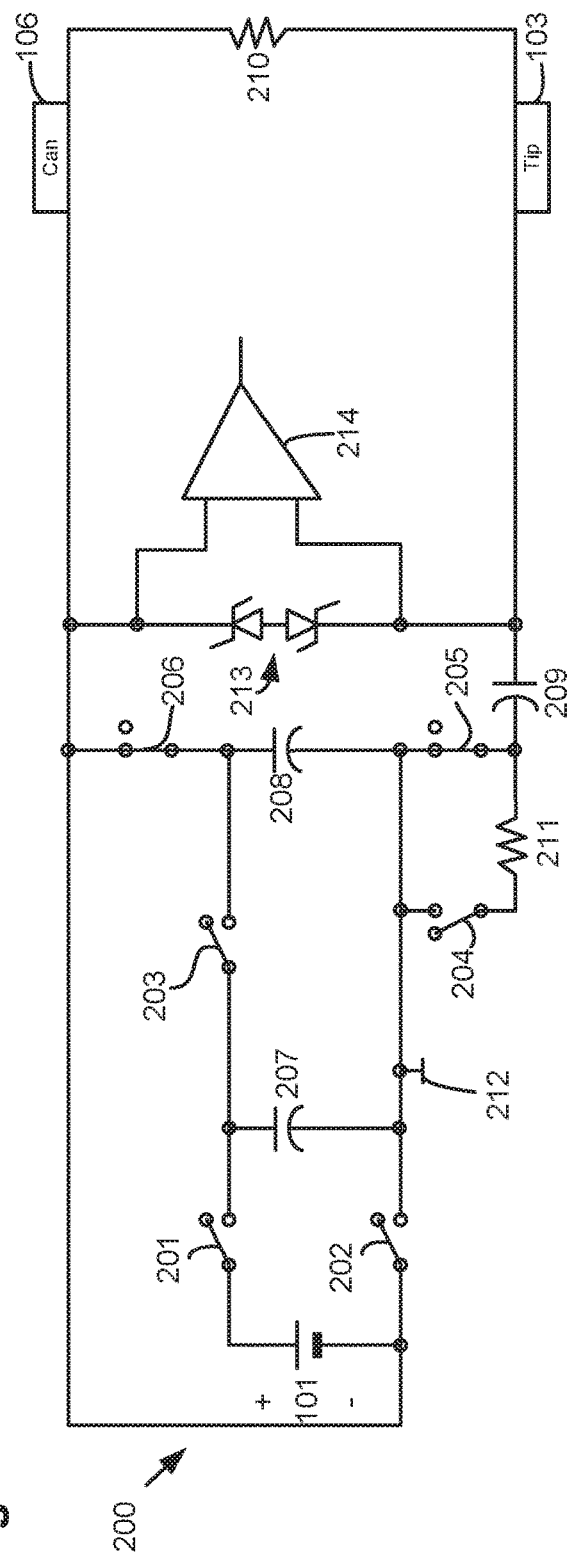

FIGS. 2A-2B are simplified schematic diagrams of pacing and sensing circuitry 200, according to one embodiment. The pacing and sensing circuitry 200 can be all or a portion of the circuitry found in electronics 102 of FIG. 1. Reference to can electrode 106 and tip electrode 103 can also be referring to the electrodes of FIG. 1.

In the illustrated embodiment, the pacing and sensing circuitry 200 can be a single p-type substrate ASIC. This circuitry allows the tip electrode of a pacemaker to be driven negative with respect to the can electrode when constrained to using a p-type substrate and a lithium CFx cell. FIG. 2A shows switches 201-206 in a first state, occurring between stimulation pulses, with switches 201-204 closed and switches 205-206 opened. FIG. 2B shows switches 201-206 in a second state, occurring while delivering a stimulation pulse, with switches 201-204 opened and switches 205-206 closed.

In the first state, energy source 101 (which can be the energy source 101 from FIG. 1) charges cell tank capacitor 207 and pacing tank capacitor 208, through switches 201-203.

In the second state, the energy source 101 is switched out of the circuit and pacing tank capacitor 208 discharges through switches 205-206 through body load 210 and output coupling capacitor 209, forcing the tip electrode 103 to go negative with respect to the can electrode 106. When the biostimulator 100 described above operates in the second state, stimulation current flows from the can electrode (positive electrode, also shown as cell housing 106 in FIG. 1) to the electrode tip (negative electrode, shown as tip electrode 103 in FIG. 1).

Returning to the first state, output coupling capacitor 209 discharges through switches 202 and 204, and body load 201. This ensures charge balance through the electrodes. Resistor 211 represents the on-resistance of switch 204, selected to limit this charge-balancing current. The resistance of resistor 211 can be chosen based on several factors, including the stimulation frequency, load impedance, and effective output capacitance.

Integrated circuit ground 212 consequently is the most negative voltage in the system. During the stimulation pulse (e.g., when the circuit is in the second state), the negative terminal of energy source 101 "flies up" from ground to the stimulating voltage on the positive terminal of pacing tank capacitor, and the positive terminal of energy source 101 "flies up" even higher but is disconnected. Cell tank capacitor 207 maintains a supply voltage for other circuits (not shown). After completion of the stimulation pulse, the cell "flies down" so that its negative terminal is reconnected to ground and its positive terminal is reconnected to the positive terminal of cell tank capacitor 207. This "flying cell" configuration permits the cell negative terminal—the negative cell housing or can electrode—to serve as the positive ring or can for stimulation.

Protection device or devices 214 limit voltage between the can electrode 106 (which is the negative terminal of energy source 101) and the tip electrode 103, to protect the circuit 200 during defibrillation or electrosurgery. The circuit 200 may include a sensing amplifier as the protection device 214 to detect intrinsic or evoked activity in the stimulated organ. The amplifier can detect potentials between tip 103 and can 106 (housing of energy source 101), and all circuitry in the amplifier can operate above ground potential 212.

A capacitive or inductive voltage converter (not shown) may optionally replace switch 203 to provide efficient charging of pacing capacitor 208 at voltages different from that of energy source 101, as is known in the art.

Figure 3:
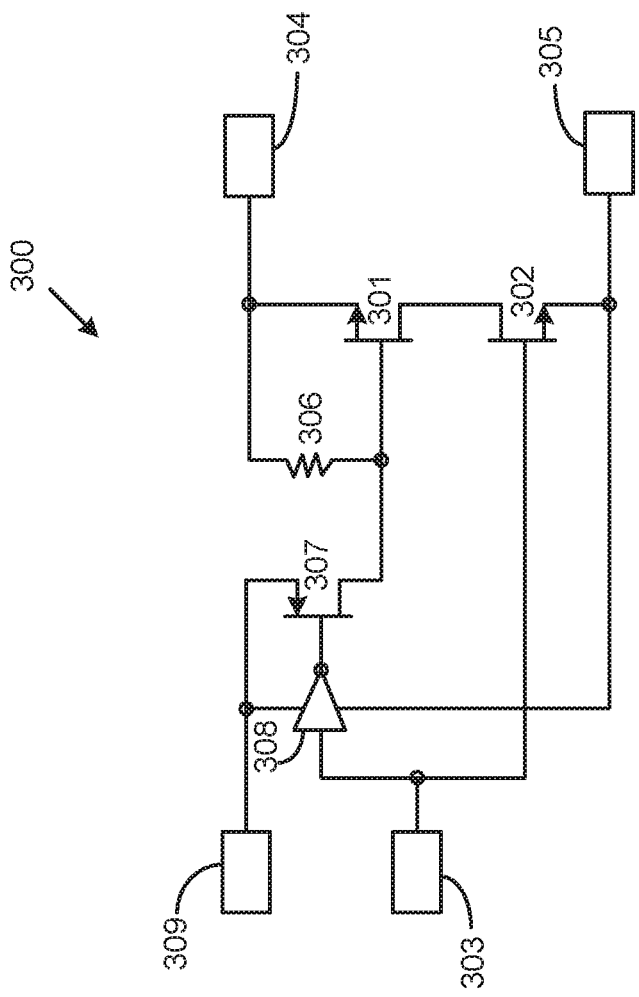
FIGS. 3 and 4 provide detailed diagrams of the implementation of switches in the pacing electronics of FIGS. 2A-2B.

FIG. 3 shows a simplified schematic diagram 300 corresponding to each of switches 204 and 205 from FIGS. 2A-2B, which require a novel implementation because of potential presence of defibrillation or electrosurgery voltages on the tip electrode (such as tip electrode 103 described above). Each switch has a high terminal 304, low terminal 305, control terminal 303, and driver voltage 309. The switch is designed to pass no current in the presence of defibrillation or electrosurgery voltages on the high terminal 304 as limited by protection devices in the circuit (such as protection device 214 above).

When control terminal 303 is low, resistor 306 holds switch 301 off and control terminal 303 holds switch 302 off, even with full protected voltage on 304. Because switches 301 and 302 are connected in opposite configurations, their body diodes do not conduct. When control terminal 303 is driven to the driver voltage 309 (for example, the voltage at the positive terminal of cell tank capacitor 207 from FIGS. 2A-2B), switch 302 turns on, and switches 308 and 307 turn switch 301 on.

Figure 4:
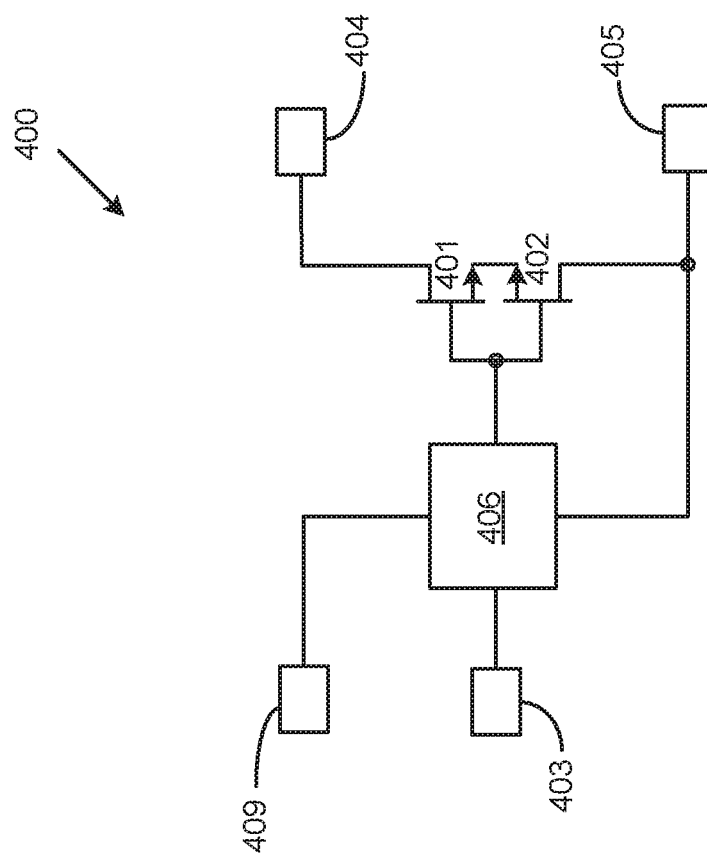

FIG. 4 shows a simplified schematic diagram 400 of switch 206 from FIGS. 2A-2B, which requires novel implementation because of potential presence of defibrillation or electrosurgery voltages on the can electrode (such as housing 106 described above). The switch has a high terminal 404, low terminal 405, control terminal 403, and driver voltage 409. The switch is designed to pass no current in the presence of defibrillation or electrosurgery voltages on the high terminal 404 as limited by protection device 214. When control terminal 403 is low (at the voltage of 405), level shifter 406 output is at the voltage of 405, which holds switches 401 and 402 off, even with full protected voltage on 404. Because switches 401 and 402 are connected in opposite configurations, their body diodes do not conduct. When control terminal 403 is driven to the driver voltage 409 (in this case the voltage at the positive terminal of energy source 101, which during stimulation is higher than the can electrode voltage), then switches 401 and 402 turn on.

Switches 201 and 203 of FIGS. 2A-2B may each be implemented with a P-channel MOSFET, and switch 202 may be implemented with an N-channel MOSFET, all in a conventional manner.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of operating a leadless pacemaker that comprises pacing electronics, a cell disposed within a cell housing, and a tip electrode that is electrically isolated from the cell housing by an insulator, the method comprising:
    during a first state
        coupling a negative terminal of the cell to the cell housing of the leadless pacemaker;
        coupling a positive terminal of the cell to the pacing electronics of the leadless pacemaker; and
        charging first and second capacitors of the leadless pacemaker; and
    during a second state, driving, with the pacing electronics, the tip electrode of the leadless pacemaker negative with respect to the cell housing during a stimulation pulse by
        electrically disconnecting the pacing electronics from the positive terminal of the cell;
        powering the pacing electronics using the first capacitor; and
        discharging the second capacitor into the cell housing, resulting in the cell housing serving as a positive electrode with respect to a negative electrode formed at the tip electrode.

2. The method of claim 1, further comprising the step of stimulating cardiac tissue with the stimulation pulse.

3. The method of claim 1, wherein the pacing electronics comprise an integrated circuit ground, wherein:
    during the first state, the negative terminal of the cell is connected to the integrated circuit ground and the positive terminal of the cell is connected to a positive terminal of the first capacitor; and
    during the second state, the negative terminal of the cell increases from a voltage level of the integrated circuit ground to a stimulating voltage due to the discharging of the second capacitor into the cell housing, and the positive terminal of the cell is disconnected from the pacing electronics.

4. The method of claim 1, wherein the pacing electronics of the leadless pacemaker, to which the positive terminal of the cell is coupled during the first state, comprises p-type substrate pacing electronics of the leadless pacemaker.

5. The method of claim 1, wherein the pacing electronics of the leadless pacemaker, to which the positive terminal of the cell is coupled during the first state, are implemented in a single p-type substrate application specific integrated circuit (ASIC).

6. The method of claim 1, wherein the coupling the negative terminal of the cell to the cell housing causes the cell housing to be used as a ring or can electrode for the leadless pacemaker.

7. The method of claim 6, further comprising:
    limiting a voltage between the cell housing, which is being used as the ring or can electrode, and the tip electrode during the second state.

8. The method of claim 6, wherein:
    the coupling the negative terminal of the cell to the cell housing of the leadless pacemaker, and the coupling the positive terminal of the cell to the pacing electronics of the leadless pacemaker, during the first state, are performed by closing a first set of switches; and
    the electrically disconnecting the pacing electronics from the positive terminal of the cell, the powering the pacing electronics using the first capacitor, and the discharging the second capacitor into the cell housing, during the second state, are performed by opening the first set of switches and closing a second set of switches.

9. The method of claim 8, further comprising:
    during the second state, discharging a third capacitor through the second set of switches to cause a charge balance between the tip electrode and the cell housing, which is being used as the ring or can electrode of the leadless pacemaker.

10. A leadless pacemaker, comprising:
    pacing electronics;
    first and second capacitors;
    a tip electrode;
    a cell having a negative terminal and a positive terminal; and
    a cell housing within which the cell is disposed;
    wherein during a first state
        the negative terminal of the cell is coupled to the cell housing;
        the positive terminal of the cell is coupled to the pacing electronics; and
        the first and second capacitors are being charged; and
    wherein during a second state,
        the tip electrode is driven negative with respect to the cell housing during a stimulation pulse by
            electrically disconnecting the pacing electronics from the positive terminal of the cell;
            powering the pacing electronics using the first capacitor; and
            discharging the second capacitor into the cell housing, resulting in the cell housing becoming a positive electrode with respect to a negative electrode formed at the tip electrode.

11. The leadless pacemaker of claim 10, wherein:
    the pacing electronics include an integrated circuit ground;
    during the first state, the negative terminal of the cell is connected to the integrated circuit ground and the positive terminal of the cell is connected to a positive terminal of the first capacitor; and
    during the second state, the negative terminal of the cell increases from a voltage level of the integrated circuit ground to a stimulating voltage due to the discharging of the second capacitor into the cell housing, and the positive terminal of the cell is disconnected from the pacing electronics.

12. The leadless pacemaker of claim 10, wherein the pacing electronics of the leadless pacemaker, to which the positive terminal of the cell is coupled during the first state, comprise p-type substrate pacing electronics of the leadless pacemaker.

13. The leadless pacemaker of claim 10, wherein the pacing electronics of the leadless pacemaker, to which the positive terminal of the cell is coupled during the first state, are implemented in a single p-type substrate application specific integrated circuit (ASIC).

14. The leadless pacemaker of claim 10, wherein during the first state, the negative terminal of the cell being coupled to the cell housing causes the cell housing to act as a ring or can electrode for the leadless pacemaker.

15. The leadless pacemaker of claim 14, further comprising:
    a first set of switches; and
    a second set of switches;

wherein the first set of switches are closed during the first state to thereby couple the negative terminal of the cell to the cell housing, and couple the positive terminal of the cell to the pacing electronics; and wherein the first set of switches are opened and the second set of switches are closed during the second state, to thereby electrically disconnect the pacing electronics from the positive terminal of the cell, power the pacing electronics using the first capacitor, and discharge the second capacitor into the cell housing.

16. The leadless pacemaker of claim 15, further comprising:

a third capacitor that during the second state is discharged through the second set of switches to cause a charge balance between the tip electrode and the cell housing, which is acting as the ring or can electrode of the leadless pacemaker.

17. The leadless pacemaker of claim 10, further comprising:

an insulator that electrically isolates the tip electrode from the cell housing;

wherein the leadless pacemaker does not include an additional housing or ring electrode disposed around the cell housing.

18. The leadless pacemaker of claim 10, wherein the pacing electronics are configured to permit the cell housing, which is coupled to the negative terminal of the cell, to serve as a positive ring or can electrode during the stimulation pulse.

19. A method of operating a leadless pacemaker that comprises a cell disposed within a cell housing and a tip electrode that is electrically isolated from the cell housing by an insulator, the method comprising:

during a first state, coupling a negative terminal of the cell to the cell housing of the leadless pacemaker, coupling a positive terminal of the cell to pacing electronics of the leadless pacemaker, and charging first and second capacitors of the leadless pacemaker; and during a second state, electrically disconnecting the pacing electronics from the positive terminal of the cell, powering the pacing electronics using the first capacitor, and discharging the second capacitor into the cell housing, to thereby cause the cell housing to become positive with respect to the tip electrode during a stimulation pulse.

\* \* \* \* \*